United States Patent [19]

Effland et al.

[11] Patent Number: 4,959,377
[45] Date of Patent: Sep. 25, 1990

[54] PHENOXYPYRIDINAMINE COMPOUNDS WHICH ARE USE AS A DERMATOLOGICAL COMPOSITION

[75] Inventors: Richard C. Effland; Joseph T. Klein, both of Bridgewater; Gordon E. Olsen, Somerset; Larry Davis, Sergeantsville, all of N.J.

[73] Assignee: Hoechst-Roussel Pharmaceuticals Inc., Somerville, N.J.

[21] Appl. No.: 372,970

[22] Filed: Jun. 29, 1989

[51] Int. Cl.$^5$ .................. C07D 213/30; A61K 31/44
[52] U.S. Cl. .................................... 514/349; 546/297
[58] Field of Search .................. 546/297; 514/349

[56] References Cited

U.S. PATENT DOCUMENTS

| | | | |
|---|---|---|---|
| 3,118,884 | 1/1964 | Clark | 544/34 |
| 3,495,969 | 2/1970 | Driscoll et al. | 546/297 |
| 3,576,616 | 4/1971 | Nowotny | 71/76 |
| 3,721,676 | 3/1973 | Witzel | 546/297 |
| 3,835,143 | 9/1974 | Witzel et al. | 546/297 |

FOREIGN PATENT DOCUMENTS

| | | | |
|---|---|---|---|
| 0069885 | 9/1987 | Australia | 546/297 |
| 0110405 | 6/1984 | European Pat. Off. | 546/297 |
| 2073736 | 10/1981 | United Kingdom | 546/297 |

OTHER PUBLICATIONS

Brewster et al., J. Heterocyclic Chem., vol. 15, 1975, p. 1497.
Butter et al., J. Med. Chem., vol. 24, 1981, pp. 346–350.
Ito et al., Pharm. Bull., vol. 26, No. 5, 1978, pp. 1375–1383.

Primary Examiner—Mary C. Lee
Assistant Examiner—Zinna Northington-Davis
Attorney, Agent, or Firm—Tatsuya Ikeda

[57] ABSTRACT

There are described compounds of the formula

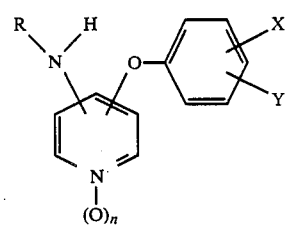

where
  n is 0 or 1;
  X is hydrogen, loweralkyl, loweralkoxy, halogen, formyl, loweralkylcarbonyl, loweralkyoxycarbonyl, loweralkoxycarbonylloweralkyl or hydroxymethyl;
  Y is hydrogen or halogen; and
  R is hydrogen, loweralkyl aryllower alkyl or loweralkylcarbonyl, which compounds are useful as topical antiinflammatory agents for the treatment of various dermatoses.

30 Claims, No Drawings

PHENOXYPYRIDINAMINE COMPOUNDS WHICH ARE USE AS A DERMATOLOGICAL COMPOSITION

The present invention relates to compounds of Formula I,

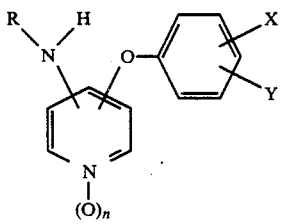

where
n is 0 or 1;
X is hydrogen, loweralkyl, loweralkoxy, halogen, formyl, loweralkylcarbonyl, loweralkoxycarbonyl, loweralkoxycarbonylloweralkyl or hydroxymethyl;
Y is hydrogen or halogen; and
R is hydrogen, loweralkyl, arylloweralkyl or loweralkylcarbonyl,
which compounds are useful as topical antiinflammatory agents for the treatment of various dermatoses including, for example, exogenous dermatitides (e.g. sunburn, photoallergic dermatitis, urticaria, contact dermatitis, allergic dermatitis), endogenous dermatitides (e.g. atopic dermatitis, seborrheic dermatitis, nummular dermatitis), dermatitides of unknown etiology (e.g. generalized exfoliative dermatitis), and other cutaneous disorders with an inflammatory component (e.g. psoriasis).

Also included within the scope of this invention are compounds of Formula II where n, X and Y as defined above, which are useful for the same dermatological applications as mentioned above and also as direct precursors of the compounds of Formula I.

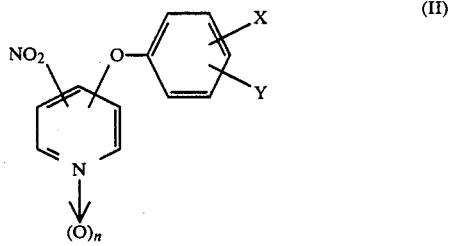

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term halogen shall mean fluorine, chlorine, bromine or iodine.

The term aryl shall mean a phenyl group optionally mono-substituted with a loweralkyl, loweralkoxy, halogen or trifluoromethyl group.

Throughout the specification and the appended claims, a given chemical formula or name shall encompass all stereo, optical, geometrical and tautomeric isomers where such isomers exist.

The compounds of this invention are prepared by utilizing one or more of the synthetic steps described below.

Throughout the description of the synthetic steps, the notations n, X, Y and R shall have the respective meanings given above unless otherwise stated or indicated, and other notations shall have the respective meanings defined in their first appearances unless otherwise stated or indicated.

STEP A:

A compound of Formula III where Hal is F or Cl, preferably F, is allowed to react with a compound of Formula IV where M=Na, Li or K to afford a compound of Formula II.

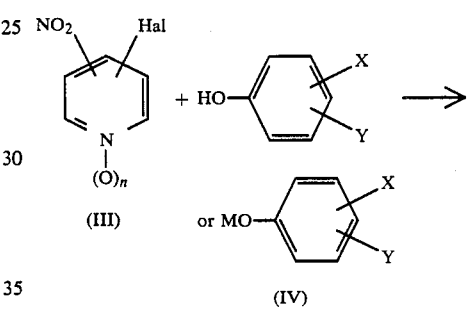

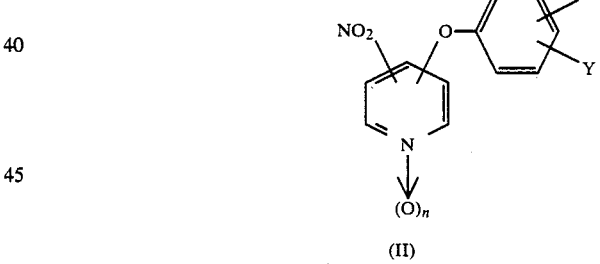

This reaction is typically conducted in a suitable solvent such as ethanol, dimethylformamide, dimethylsulfoxide or N-methylpyrrolidone at a temperature of about 0° to 150° C.

3-Fluoro-4-nitropyridine-1-oxide, which belongs to the group of compounds of Formula III, is disclosed in Talik and Talik, Roczniki Chemii, Volume 38, 777 (1964). 4-Chloro-3-nitropyridine, which also belongs to the group of compounds of Formula III, is disclosed in Talik and Talik, Roczniki Chemii, Volume 43, 923 (1969).

STEP B:

A compound of Formula IIa is selectively hydrogenated to afford a compound of Formula V.

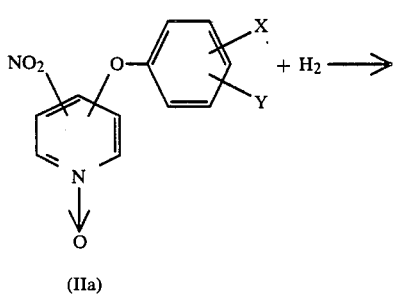

(IIa)

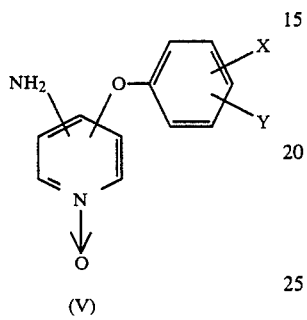

(V)

This selective hydrogenation is typically conducted with the aid of a suitable catalyst such as Pd/C or PtO$_2$ and a suitable medium such as ethanol at a temperature of about 20° to 100° C.

STEP C:

Compound IIa is catalytically hydrogenated in a manner similar to the one described in STEP B above, except that a longer reaction period or higher reaction temperature is preferably employed, to afford a compound of Formula VI.

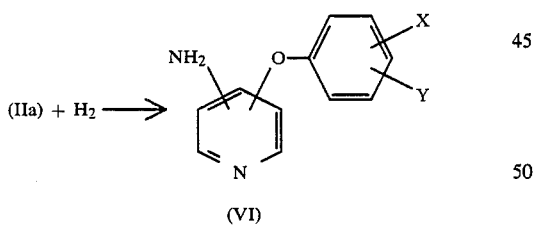

(VI)

Instead of using compound IIa in the above reaction, one can also use compound V and conduct the hydrogenation in substantially the same manner as described above to obtain compound VI.

STEP D:

A compound of Formula VII obtained from STEP B or C is allowed to react with a compound of the formula, R$_1$-Hal, where R$_1$ is loweralkyl, arylloweralkyl or loweralkylcarbonyl and Hal is bromine or chlorine, in a routine manner known to the art to afford a compound of Formula VIII.

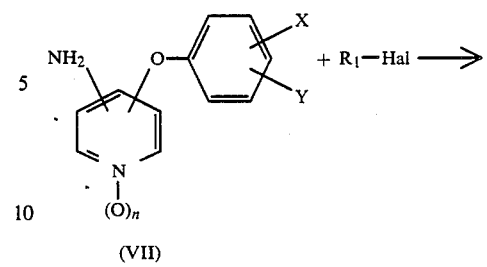

(VII)

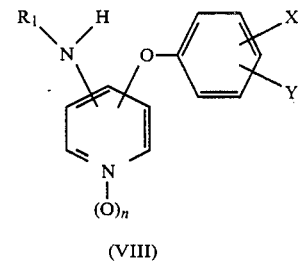

(VIII)

STEP E:

A compound of Formula IIb is catalytically hydrogenated to afford a compound of Formula IX.

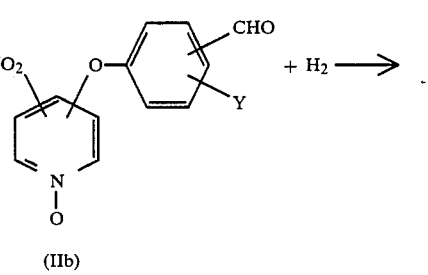

(IIb)

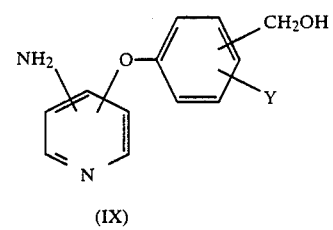

(IX)

This hydrogenation is conducted in substantially the same manner as in STEP C above.

Compounds of Formula I and Formula II according to this invention are useful as topical agents for the treatment of various skin disorders such as those mentioned earlier. The dermatological activities of the compounds of this invention were ascertained with reference to the following methods.

DERMATOLOGICAL TEST METHODS

Phospholipase A$_2$-induced Paw Edema (PIPE)

The ability of compounds to prevent naja naja (snake venom) phospholipase A$_2$-induced paw edema in male Wistar rats (100–125 g) was measured. PLA$_2$ (3 units/paw) alone or with 0.1M of the test compound was injected in the subplantar region of the rat left hindpaw. Immediately subsequent to the injection and at two hours post administration the paw was immersed in a mercury bath, and paw displacement was measured on a recorder via a transducer. (Standard: hydrocortisone $ED_{50}=0.46M$). See Giessler, A. J. et al., Agents and Actions, Vol. 10, Trends in Inflammation Research (1981), p. 195.

In Vitro Phospholipase $A_2$ Assay ($PLA_2$)

The ability of a compound to modulate $PLA_2$ activity (cleavage of $^{14}$C-dipalmitoyl phosphotidylcholine at the 2-position to $^{14}$C-palmitic acid) was quantitated in this assay. The reaction mixture contained Tris buffer (25 mM), pH 8.0, calcium chloride (2.0 mM), bovine serum albumin (0.5 mg), dipalmitoyl phosphotidylcholine ($8 \times 10^{-5}$M), ($^{14}$C-palmitoyl)dipalmitoyl phosphotidylcholine ($6 \times 10^3$ cpm), porcine pancreatic $PLA_2$ (3.2 units) and the test compound. The reaction was run at 37° C. in a shaking incubator. The reaction was quenched and an internal standard was added in order to determine sample recovery. The samples were loaded onto $C_{18}$ columns, eluted with ethanol, and the radioactivity was then measured. (Standard: quinacrine $IC_{50}=3.5 \times 10^{-4}$M). See Feyen, J. H. M., et al., Journal of Chromatography 259 (1983), pp. 338–340.

Arachidonic Acid-Induced Ear Edema (AAEE)

The purpose of this assay was to determine the ability of a topically-applied compound to prevent mouse ear edema induced by topical application of arachidonic acid. Female Swiss Webster mice topically received vehicle or test compound (1.0 mg/ear) on both ears (10 μl on outer and inner ears). After 30 minutes, the right ear of all groups received arachidonic acid (4 mg/ear) and the left ear received vehicle alone. After an additional 1 hour, the mice were sacrificed and an ear punch (4 mm) was taken from each ear. The difference in right and left ear punch weights for each animal was determined to assess activity. (Standard: indomethacin $ED_{50}=1.5$ mg/ear). See Young, J. M. et al., J. Invest. Dermatol., 80, (1983), pp 48–52.

TPA-Induced Ear Edema (TPAEE)

The purpose of this assay was to determine the ability of a topically-applied compound to prevent ear edema induced by topical application of TPA (phorbol 12-myristate acetate). Female Swiss Webster mice topically received TPA (10 μg/ear) on the right ear and vehicle on the left ear. The test compound (10 μg/ear) was applied to both ears. After five hours, the animals were sacrificed and an ear punch (4 mm) was taken from each ear. The difference in right and left ear punch weights for each animal was determined to assess activity. (Standard: hydrocortisone $ED_{50}=47$ μg/ear). See Young, J. M. et al., J. Invest. Dermatol., 80 (1983), pp. 48–52.

Dermatological activities for some of the compounds of this invention are presented in Table 1.

TABLE 1

| Compound | PIPE* (0.1 M) | PLA$_2$* (0.01 M) | AAEE (1 mg) | TPAEE (10 μg) |
|---|---|---|---|---|
| 3-(4-methoxy-phenoxy)-4-nitropyridine-1-oxide | | | | −43% |
| 3-phenoxy-4-pyridinamine hydrochloride | −79% | −95% | −31% | −60% |
| 2-(4-amino-3-pyridinyloxy)-benzoic acid methyl ester hydrochloride | | −38% | | |

TABLE 1-continued

| Compound | PIPE* (0.1 M) | PLA$_2$* (0.01 M) | AAEE (1 mg) | TPAEE (10 μg) |
|---|---|---|---|---|
| 4-(4-amino-3-pyridinyloxy)-benzeneacetic acid ethyl ester oxalate | | | | −39% |
| 4-phenoxy-3-pyridinamine | | | | −34% |
| N-(3-phenoxy-4-pyridinyl)acetamide hydrochloride | | −73% | | |
| 2-(4-amino-3-pyridinyloxy)-benzenemethanol oxalate | | −82% | | |

*difference in edema vs. control

Examples of the compound of this invention include:
2-(4-amino-3-pyridinyloxy)benzoic acid methyl ester, N-oxide;
3-phenoxy-4-pyridinamine;
3-(4-methoxyphenoxy)-4-pyridinamine;
2-(4-amino-3-pyridinyloxy)benzoic acid methyl ester;
4-(4-amino-3-pyridinyloxy)benzeneacetic acid ethyl ester;
4-phenoxy-3-pyridinamine;
N-(3-phenoxy-4-pyridinyl)acetamide;
2-(4-amino-3-pyridinyloxy)benzenemethanol;
3-(4-ethoxyphenoxy)-4-pyridinamine;
2-(4-methylamino-3-pyridinyloxy)benzoic acid methyl ester;
2-(3-amino-4-pyridinyloxy)benzoic acid methyl ester;
2-(4-amino-3-pyridinyloxy)benzeneacetic acid methyl ester;
4-nitro-3-phenoxypyridine-1-oxide;
3-(4-methoxyphenoxy)-4-nitropyridine-1-oxide;
2-(4-nitro-3-pyridinyloxy)benzoic acid methyl ester, N-oxide;
5-chloro-2-(4-nitro-3-pyridinyloxy)benzoic acid methyl ester, N-oxide;
2-(4-nitro-3-pyridinyloxy)benzaldehyde, N-oxide;
1-[2-(4-nitro-3-pyridinyloxy)phenyl]ethanone, N-oxide;
4-(4-nitro-3-pyridinyloxy)benzeneacetic acid ethyl ester, N-oxide;
3-nitro-4-phenoxypyridine;
3-(4-ethoxyphenoxy)-4-nitropyridine-1-oxide;
2-(4-nitro-3-pyridinyloxy)benzeneacetic acid methyl ester;

The following examples are presented in order to illustrate this invention:

EXAMPLE 1

4-Nitro-3-phenoxypyridine-1-oxide

Phenol (4.2 g) in 10 ml dimethylformamide (DMF) was added to an ice-cooled suspension of sodium hydride (1.08 g) in 10 ml dimethylformamide. After the anion formation, a solution of 3-fluoro-4-nitropyridine-1-oxide[1] (6.5 g) in 30 ml dimethylformamide was added. After thirty minutes, the reaction mixture was stirred with ice-water and extracted with dichloromethane. The organic extract was washed with water and saturated sodium chloride solution, dried (anhy. MgSO$_4$), filtered and concentrated to 14 g waxy solid which was triturated with ether to give 7.5 g solid, m.p. 110°–113°. A 4 g sample was recrystallized from absolute ethanol to give 3.6 g solid, m.p. 110°–111°.

[1] Talik and Talik, Roczniki Chemii 38, 777 (1964).

ANALYSIS: Calculated for $C_{11}H_8N_2O_4$: 56.90% C; 3.47% H; 12.07% N; Found: 56.86% C; 3.44% H; 12.08% N.

EXAMPLE 2

3-(4-Methoxyphenoxy)-4-nitropyridine-1-oxide

To 75 ml DMF were added 4-methoxyphenol (5.0 g) and $Na_2CO_3$ (8.0 g). After stirring at ambient temperature for fifteen minutes, a solution of 3-fluoro-4-nitropyridine-1-oxide (6.0 g) in 25 ml DMF was added in fifteen minutes.

After stirring at ambient temperature for five hours, the mixture was poured into 400 ml water, stirred for five minutes, and extracted with ethyl acetate (3 x). The organic layer was washed with water (2x) and dried (saturated NaCl, anhydrous $MgSO_4$).

After filtration, the solvent was evaporated to yield 10 g of solid, m.p. 90° C., which was eluted on a silica gel column with 5% ethyl acetate/dichloromethane via HPLC. The desired fractions were combined and concentrated to a solid, 9.0 g, m.p. 104°–108° C. A 3.0 g sample of this material was recrystallized from methanol/ether (1:20) to give 2.3 g needles, m.p. 109°–110° C.

ANALYSIS: Calculated for $C_{12}H_{10}N_2O_5$: 54.97% C; 3.84% H; 10.68% N. Found: 55.06% C; 3.69% H; 10.66% N.

EXAMPLE 3

2-(4-Nitro-3-pyridinyloxy)benzoic acid methyl ester, N-oxide

Methyl salicylate (10.6 g) in 50 ml dimethylformamide was slowly added to an ice-cooled suspension of NaH (1.68 g) in 5 ml dimethylformamide. After the anion formation, a solution of 3-fluoro-4-nitropyridine-1-oxide (10 g) in 50 ml dimethylformamide was added. After one hour the reaction mixture was stirred with ice-water and extracted with dichloromethane. The organic extract was washed with water and saturated sodium chloride solution, dried (anhy. $MgSO_4$), filtered and concentrated to 22 g oil which was crystallized from ethanol to give 15 g crystals, m.p. 108°–110°. Three grams were recrystallized from absolute ethanol to give 2.7 g crystals, m.p. 114°–115°.

ANALYSIS: Calculated for $C_{13}H_{10}N_2O_6$: 53.80% C; 3.47% H; 9.65% N. Found: 53.76% C; 3.53% H; 9.69% N.

EXAMPLE 4

5-Chloro-2-(4-nitro-3-pyridinyloxy)benzoic acid methyl ester, N-oxide

A solution of 5-chlorosalicyclic acid methyl ester (6.5 g) in 25 ml dimethylformamide was added to an ice-cooled suspension of sodium hydride (0.84 g) in 5 ml dimethylformamide. After the anion formation, a solution of 3-fluoro-4-nitropyridine-1-oxide (5 g) in 25 ml dimethylformamide was added. After one hour the reaction mixture was stirred with ice-water and extracted with dichloromethane. The organic extract was washed with water and saturated sodium chloride solution, dried (anhydrous $MgSO_4$), filtered and concentrated to 10.5 g oil. This oil was crystallized from absolute ethanol to give 8 g crystals, m.p. 155°–158°. Three grams were recrystallized from absolute ethanol to give 2.8 g crystals, m.p. 158°–160°.

ANALYSIS: Calculated for $C_{13}H_9ClN_2O_6$: 48.09% C; 2.79% H; 8.63% N. Found: 48.05% C; 2.74% H; 8.62% N.

EXAMPLE 5

2-(4-Nitro-3-pyridinyloxy)benzaldehyde, N-oxide

Salicylaldehyde (4.2 g) in 10 ml dimethylformamide was added to an ice-cooled suspension of sodium hydride (0.84 g) in 5 ml dimethylformamide. After the anion formation, a solution of 3-fluoro-4-nitropyridine-1-oxide (5 g) in 15 ml dimethylformamide was added. After thirty minutes, the reaction mixture was stirred with ice-water and extracted with dichloromethane. The organic extract was washed with water and saturated sodium chloride solution, dried (anhy. $MgSO_4$), filtered and concentrated to 9 g oil. This oil was crystallized from hot absolute ethanol to give 7.5 g crystals, m.p. 122°–123°.

ANALYSIS: Calculated for $C_{12}H_8N_2O_5$: 55.39% C; 3.10% H; 10.77% N. Found: 55.21% C; 2.99% H; 10.69% N.

EXAMPLE 6

1-[2-(4-Nitro-3-pyridinyloxy)phenyl]ethanone, N-oxide

A solution of 1-(2-hydroxy)phenylethanone (4.7 g) in 20 ml dimethylformamide was slowly added to an ice-cooled suspension of sodium hydride (0.84 g) in 5 ml dimethylformamide. After the anion formation, a solution of 3-fluoro-4-nitropyridine-1-oxide (5 g) in 20 ml dimethylformamide was added. After thirty minutes, the reaction mixture was stirred with ice-water and extracted with dichloromethane. The organic extract was washed with water and saturated sodium chloride solution, dried (anhy. $MgSO_4$), filtered and concentrated to 9 g oil. This oil was purified by flash chromatography (silica, ethyl acetate) to give 8 g solid, m.p. 100°–103°. Six grams were recrystallized from ethanol to give 4 g crystals, m.p. 113°–115°.

ANALYSIS: Calculated for $C_{13}H_{10}N_2O_5$: 56.93% C; 3.68% H; 10.22% N. Found: 56.96% C; 3.64% H; 10.36% N.

EXAMPLE 7

4-(4-Nitro-3-pyridinyloxy)benzeneacetic acid ethyl ester, N-oxide

To a solution of 4-hydroxyphenylacetic acid ethyl ester (6.0 g) in 50 ml DMF, was added $Na_2CO_3$ (5.0 g). After stirring at ambient temperature for five minutes, a solution of 3-fluoro-4-nitropyridine-1-oxide (5.0 g) in 25 ml DMF was added in ten minutes.

After stirring at ambient temperature for four hours, the mixture was filtered, and the filtrate poured into 200 ml water, stirred for five minutes, and extracted with ethyl acetate (3x). The organic layer was washed with water (2x) and dried (saturated NaCl, anhydrous $MgSO_4$).

After filtration, the solvent was evaporated to afford an oil (11 g), which was eluted on a silica gel column with 50% ethyl acetate/dichloromethane via HPLC. The desired fractions were combined and concentrated to a thick oil, which solidified to 7.4 g of solid, m.p. 101°–102° C.

ANALYSIS: Calculated for $C_{15}H_{14}N_2O_6$: 56.60% C; 4.43% H; 8.80% N. Found: 56.77% C; 4.41% H; 8.69% N.

EXAMPLE 8

3-Nitro-4-phenoxypyridine

To phenol (6.5 g) in 20 ml DMF at room temperature was added K$_2$CO$_3$ (20 g) and this mixture stirred for 15 minutes at room temperature. Then 4-chloro-3-nitropyridine (10.0 g) in 60 ml DMF was added dropwise and the mixture stirred for two hours at ambient temperature. The mixture was poured into water and extracted with ethyl acetate. The organic layer was washed with water and dried (sat. NaCl, anhy. MgSO$_4$).

After filtration, the solvent was evaporated to yield an oil (15 g), which was eluted with dichloromethane (DCM) on a silica gel column via HPLC. The desired fractions were concentrated to yield an oil which solidified on standing (9.2 g). Of this material, 7.0 g was recrystallized from ethanol to yield a solid (3.3 g), m.p. 70°–73° C.

ANALYSIS: Calculated for C$_{11}$H$_8$N$_2$O$_3$: 61.11% C; 3.73% H; 12.96% N. Found: 60.98% C; 3.70% H; 12.96% N.

EXAMPLE 9

2-(4-Amino-3-pyridinyloxy)benzoic acid methyl ester, N-oxide

A solution of 2-(4-nitro-3-pyridinyloxy)benzoic acid methyl ester, N-oxide (30 g) in 1.5 L ethanol containing 1.5 g platinum oxide was hydrogenated for five hours at 50 psi. The mixture was filtered and concentrated to 26 g solid which was purified by flash chromatography (silica, 5% methanol in dichloromethane) to give 20 g of 2-(4-amino-3-pyridinyloxy)benzoic acid methyl ester and 4.5 g solid, d 200°. The latter material was purified by flash chromatography (silica, 10% methanol in dichloromethane) to give 3.4 g solid, d 200°. This material was recrystallized from ethanol/ether to give 2.5 g solid, d 200°.

ANALYSIS: Calculated for C$_{13}$H$_{12}$N$_2$O$_4$: 59.99% C; 4.65% H; 10.77% N. Found: 59.94% C; 4.60% H; 10.69% N.

EXAMPLE 10

3-Phenoxy-4-pyridinamine hydrochloride

A solution of 4-nitro-3-phenoxypyridine-1-oxide (5 g) in 500 ml absolute ethanol containing 250 mg platinum oxide was hydrogenated for six hours at 40 psi. The mixture was filtered and concentrated to 4 g oil which was converted to the hydrochloride salt in isopropanol to give 3.8 g crystals, d 240°–242°. Three grams were recrystallized from isopropanol to give 2.3 g crystals, d 247°–249°.

ANALYSIS: Calculated for C$_{11}$H$_{10}$N$_2$O•HCl: 59.33% C; 4.98% H; 12.58% N. Found: 59.14% C; 5.01% H; 12.62% N.

EXAMPLE 11

3-(4-Methoxyphenoxy)-4-pyridinamine

To 250 ml ethanol in a 500 ml Parr hydrogenation bottle, were added 3-(4-methoxyphenoxy)-4-nitropyridine-1-oxide (7.9 g) and 0.4 g PtO$_2$. After shaking for two hours at fifty psi of hydrogen, the mixture was filtered and concentrated to 5.8 g of oil.

This oil was eluted on a silica gel column with 5% methanol/DCM via HPLC. The desired fractions were combined and concentrated to solid, 4.3 g, m.p. 97°–99° C. A 3.0 g sample was recrystallized from ether to give 2.3 g of solid, m.p. 100°–101° C.

ANALYSIS: Calculated for C$_{12}$H$_{12}$N$_2$O$_2$: 66.65% C; 5.59% H; 12.95% N. Found: 66.63% C; 5.66% H; 12.92% N.

EXAMPLE 12

2-(4-Amino-3-pyridinyloxy)benzoic acid methyl ester hydrochloride

A solution of 2-(4-nitro-3-pyridinyloxy)benzoic acid methyl ester, N-oxide (12 g) in 500 ml absolute ethanol containing 1 g platinum oxide was hydrogenated for two hours at 40 psi. The mixture was filtered and concentrated to 11 g solid, m.p. 133°–135°. This material was purified by flash chromatography (silica, 5% methanol in dichloromethane) to give 9 g solid, m.p. 136°–138°. A 2.5 g sample was converted to the hydrochloride salt and recrystallized twice from isopropanol/ether to give 2.1 g crystals, d 212°–213°.

ANALYSIS: Calculated for C$_{13}$H$_{12}$N$_2$O$_3$•HCl: 55.62% C; 4.67% H; 9.98% N. Found: 55.36% C; 4.70% H; 9.99% N.

EXAMPLE 13

4-(4-Amino-3-pyridinyloxy)benzeneacetic acid ethyl ester oxalate

To a 500 ml Parr hydrogenation bottle containing 250 ml of absolute ethanol were added 4-(4-nitro-3-pyridinyloxy)-benzeneacetic acid ethyl ester, N-oxide (4.3 g) and 0.5 g PtO$_2$.

After shaking under hydrogen for two hours, the mixture was filtered and the filtrate concentrated to an oil (4.0 g). This oil was eluted on a silica gel column with 10% methanol/DCM via HPLC. The desired fractions were combined and concentrated to an oil (1.4 g). This oil was dissolved in hot ethanol, the pH adjusted to 1 with an ethanolic oxalic acid solution, and the solution was diluted with ether. The resultant precipitate was collected and dried to give 1.5 g, m.p. 175° C. (dec.).

ANALYSIS: Calculated for C$_{15}$H$_{16}$N$_2$O$_3$•C$_2$H$_2$O$_4$: 56.35% C; 5.01% H; 7.73% N. Found: 55.90% C; 4.95% H; 7.60% N.

EXAMPLE 14

4-Phenoxy-3-pyridinamine

To a slurry of 10% Pd/C in 5 ml of absolute ethanol was added 3-nitro-4-phenoxypyridine (7.5 g) in 245 ml of ethanol. This mixture was shaken on a Parr apparatus for two hours. The mixture was filtered and the filtrate concentrated to yield an oil (6.4 g) which was eluted with ethyl acetate on a silica gel column in HPLC. The desired fractions were concentrated to yield an oil (4.5 g). This material was distilled using a Kugelrohr apparatus to yield an oil (1.8 g).

ANALYSIS: Calculated for C$_{11}$H$_{10}$N$_2$O: 70.95% C; 5.41% H; 15.04% N. Found: 70.38% C; 5.56% H; 14.86% N.

EXAMPLE 15

N-(3-Phenoxy-4-pyridinyl)acetamide hydrochloride

A solution of 4-amino-3-phenoxypyridine (5 g) in 10 ml acetic anhydride (11 g) was warmed for ten minutes on a steam bath, cooled, concentrated, stirred with ice, basified with sodium carbonate and extracted with dichloromethane. The organic extract was washed with water, dried (anhy. MgSO4), filtered and concentrated to 6 g solid. This material was purified by column chromatography (alumina, ether) to give 5.4 g solid, m.p. 127°–129°. A four gram sample was purified by flash chromatography (silica, 20% ethyl acetate in dichloromethane) to give 3.3 g solid, m.p. 128°–130°. This solid was converted to the hydrochloride salt and recrystallized twice from isopropanol/ether to give 3.2 g crystals, d 188°–190°.

ANALYSIS: Calculated for $C_{13}H_{12}N_2O_2 \cdot HCl$: 58.98% C; 4.95% H; 10.59% N. Found: 58.88% C; 4.83% H; 10.55% N.

EXAMPLE 16

2-(4-Amino-3-pyridinyloxy)benzenemethanol oxalate

A solution of 2-(4-nitro-3-pyridinyloxy)benzaldehyde, N-oxide (3.3 g) in 500 ml ethanol containing 350 mg platinum oxide was hydrogenated for seven hours at 50 psi. The mixture was filtered and concentrated to 3 g oil which was purified by flash chromatography (silica, 10% methanol in dichloromethane) to give 2 g solid, m.p. 105°–110°. This material was converted to the oxalate salt and recrystallized successively from isopropanol and ethanol to give 2 g crystals, d 148°–150°.

ANALYSIS: Calculated for $C_{12}H_{12}N_2O_2 \cdot (CO_2H)_2$: 54.90% C; 4.61% H; 9.15% N. Found: 54.76% C; 4.71% H; 9.11% N.

We claim:

1. A compound having the formula,

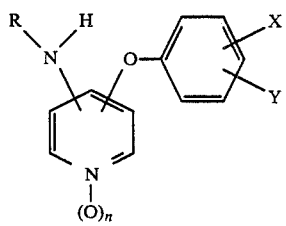

where
n is 0 or 1;
X is hydrogen, loweralkyl, loweralkoxy, halogen, formyl, loweralkylcarbonyl, loweralkoxycarbonyl, loweralkoxycarbonylloweralkyl or hydroxymethyl;
Y is hydrogen or halogen; and
R is hydrogen, loweralkyl, arylloweralkyl or loweralkylcarbonyl,
or a pharmaceutically acceptable acid addition salt thereof.

2. The compound as defined in claim 1, where Y is hydrogen.

3. The compound as defined in claim 1, where R is hydrogen or loweralkylcarbonyl.

4. The compound as defined in claim 1, where Y is hydrogen and R is hydrogen or loweralkylcarbonyl.

5. The compound as defined in claim 1, which is 2-(4-amino-3-pyridinyloxy)benzoic acid methyl ester, N-oxide.

6. The compound as defined in claim 1, which is 3-phenoxy-4-pyridinamine.

7. The compound as defined in claim 1, which is 3-(4-methoxyphenoxy)-4-pyridinamine.

8. The compound as defined in claim 1, which is 2-(4-amino-3-pyridinyloxy)benzoic acid methyl ester.

9. The compound as defined in claim 1, which is 4-(4-amino-3-pyridinyloxy)benzeneacetic acid ethyl ester.

10. The compound as defined in claim 1, which is 4-phenoxy-3-pyridinamine.

11. The compound as defined in claim 1, which is N-(3-phenoxy-4-pyridinyl)acetamide.

12. The compound as defined in claim 1, which is 2-(4-amino-3-pyridinyloxy)benzenemethanol.

13. The compound as defined in claim 1, which is 3-(4-ethoxyphenoxy)-4-pyridinamine.

14. The compound as defined in claim 1, which is 2-(4-methylamino-3-pyridinyloxy)benzoic acid methyl ester.

15. The compound as defined in claim 1, which is 2-(3-amino-4-pyridinyloxy)benzoic acid methyl ester.

16. The compound as defined in claim 1, which is 2-(4-amino-3-pyridinyloxy)benzeneacetic acid methyl ester.

17. A compound of the formula

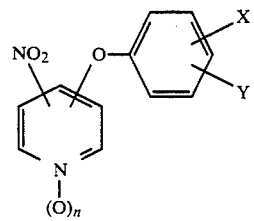

where
n is 0 or 1;
X is hydrogen, loweralkyl, loweralkoxy, halogen, formyl, loweralkylcarbonyl, loweralkoxycarbonyl, loweralkoxycarbonylloweralkyl or hydroxymethyl; and
Y is hydrogen or halogen,
with the proviso that the combination (X, Y) may not be (H, H), (H, halogen) or (halogen, halogen), the term halogen in each occurrence independently signifying fluorine, chlorine, bromine or iodine, or a pharmaceutically acceptable acid addition salt thereof.

18. The compound as defined in claim 17, where Y is hydrogen.

19. The compound as defined in claim 17, which is 3-(4-methoxyphenoxy)-4-nitropyridine-1-oxide.

20. The compound as defined in claim 17, which is 2-(4-nitro-3-pyridinyloxy)benzoic acid methyl ester, N-oxide.

21. The compound as defined in claim 17, which is 5-chloro-2-(4-nitro-3-pyridinyloxy)benzoic acid methyl ester, N-oxide.

22. The compound as defined in claim 17, which is 2-(4-nitro-3-pyridinyloxy)benzaldehyde, N-oxide.

23. The compound as defined in claim 17, which is 1-[2-(4-nitro-3-pyridinyloxy)phenyl]ethanone, N-oxide.

24. The compound as defined in claim 17, which is 4-(4-nitro-3-pyridinyloxy)benzeneacetic acid ethyl ester, N-oxide.

25. The compound as defined in claim 17, which is 3-(4-ethoxyphenoxy)-4-nitropyridine-1-oxide.

26. The compound as defined in claim 17, which is 2-(4-nitro-3-pyridinyloxy)benzeneacetic acid methyl ester, N-oxide.

27. A dermatological composition which comprises a compound as defined in claim 1 in an amount effective for treating a skin disorder, and a suitable carrier therefor.

28. A dermatological composition which comprises a compound as defined in claim 17 in an amount effective for treating a skin disorder, and a suitable carrier therefor.

29. A method of treating a patient in need of relief from a skin disorder, which comprises administering to such a patient an effective amount of a compound as defined in claim 1.

30. A method of treating a patient in need of relief from a skin disorder, which comprises administering to such a patient an effective amount of a compound as defined in claim 17.

* * * * *